United States Patent [19]

Sato et al.

[11] Patent Number: 4,681,980

[45] Date of Patent: Jul. 21, 1987

[54] METHOD FOR IMPROVING AN ELECTRICAL INSULATING HYDROCARBON

[75] Inventors: Atsushi Sato, Tokyo; Keiji Endo, Yokosuka; Shigenobu Kawakami, Ichikawa; Hitoshi Yanagishita; Shozo Hayashi, both of Yokohama, all of Japan

[73] Assignee: Nippon Petrochemicals Company Limited, Tokyo, Japan

[21] Appl. No.: 795,366

[22] Filed: Nov. 6, 1985

Related U.S. Application Data

[63] Continuation-in-part of Ser. No. 563,742, Dec. 20, 1983, abandoned.

[30] Foreign Application Priority Data

Dec. 25, 1982 [JP] Japan .................................. 57-233238
Jul. 20, 1983 [JP] Japan .................................. 58-132331

[51] Int. Cl.$^4$ .............................................. H01B 3/22
[52] U.S. Cl. ....................................... 585/6.3; 585/6.6; 585/436; 585/400; 585/444; 252/570

[58] Field of Search ................ 252/570; 585/436, 400, 585/444, 6.3, 6.6; 323/428, 429

[56] References Cited

U.S. PATENT DOCUMENTS 4,434,311  2/1984  Buss et al. ........................... 585/444

FOREIGN PATENT DOCUMENTS 0661368  11/1951  United Kingdom .
1180459   2/1970  United Kingdom .
2082626   3/1982  United Kingdom .

*Primary Examiner*—Paul Lieberman
*Assistant Examiner*—Hoa Van Le
*Attorney, Agent, or Firm*—Scully, Scott, Murphy & Presser

[57] ABSTRACT

A novel method for improving electrical insulating hydrocarbon. The electrical insulating substance is obtained by dehydrogenating aromatic hydrocarbons having two aromatic nuclei. The electrical insulating substance itself or a mixture of it with other electrical insulating oils is suitable for use in impregnation of electrical appliances.

5 Claims, No Drawings

METHOD FOR IMPROVING AN ELECTRICAL INSULATING HYDROCARBON

CROSS-REFERENCE TO RELATED APPLICATION

This application is a continuation-in-part of application Ser. No. 563,742, filed Dec. 20, 1983 now abandoned.

BACKGROUND OF THE INVENTION
1. Field of the Invention

This invention relates to a method for improving the electrical characteristics of an electrical insulating hydrocarbon.

More specifically, the invention relates to a method for improving the electrical characteristics of an electrical insulating hydrocarbon. The improved electrical insulating hydrocarbon of the present invention is suitable for use in oil-filled or oil-impregnated electrical appliances in which insulating materials or dielectric materials made of plastics, such as polyolefin, are at least partly employed.

2. Description of the Prior Art

Electrical appliances such as oil-filled capacitors, oil-filled power cables and transformers have recently been made to withstand high electric voltages while being small in size. With this tendency, various kinds of plastic films are used together with conventional insulating paper.

There are several electrical insulating hydrocarbon oils known that are filled in or impregnated in these electrical applicances. However, the conventional electrical insulating oils such as refined mineral oils, polybutenes, alkylbenzenes, diarylalkanes, diarylcycloalkanes, arylindanes, alkylbiphenyls, cycloalkylbiphenyls, alkylnaphthalenes and cycloalkylnaphthalenes have several drawbacks. Further, conventional electrical insulating hydrocarbon oils are not completely compatible with the above-mentioned plastic materials, such as polyolefin films, which have recently come into use in oil-filled electrical appliances.

With the requirements of high-voltage durability and size reduction, it is necessary that the electrical insulating oil have a high dielectric breakdown voltage, a low dielectric loss tangent, and good hydrogen gas absorbing capacity. The hydrocarbon gas absorbing capacity indicates the stability of the insulating oil against corona discharge (partial discharge) under high electric voltage conditions. The higher the gas-absorbing capacity, the smaller the likelihood of corona discharge, which means that the insulating oil has excellent stability and/or durability.

In order to meet the requirement of high-voltage use, plastic films such as polyolefins films, polystyrene films and polyester films are used to either partially or completely replace the conventional insulating paper as insulating materials or dielectric materials for electrical appliances such as oil-filled electric cables and capacitors. In view of their dielectric strength, dielectric loss tangent and dielectric constant, polyolefin films especially polypropylene and cross-linked polyethylene films, are preferred insulating or dielectric materials.

When these polyolefin films are impregnated with insulating oils, some oils cause the films to swell to some extent. If a film becomes swollen, the thickness of the insulating layer increases. As a result, the resistance to the flow of insulating oil increases in electrical cables, and insufficient impregnation with insulating oil occurs in electric capacitors. This causes the formation of voids (un-impregnated portions) and the undesirable effect or lowering of the corona discharge voltage.

In connection with the above-mentioned conventional electrical insulating oils, the values of the dielectric breakdown voltages (BDV) and the dielectric loss tangents (tanδ) are satisfactory to a certain extent, but the hydrogen gas absorbing capacity or corona discharge characteristics and the stability of the dimensions of the polypropylene films are not satisfactory.

British Pat. No. 2,082,626 to Sato, et al. describes an electrical insulating oil that comprises aromatic hydrocarbons having two aromatic nuclei, such as diarylalkanes. The insulating oil is prepared by adding unsaturated dimers of styrene or its methyl homolog to diarylalkanes.

U.S. Pat. No. 4,111,824 to Schulz, et al. describes an electrical insulating oil prepared from the heavy oil fraction obtained as a by-product in the preparation of ethylbenzene. The insulating oil is recovered by distillation from a fraction which contains diarylalkanes.

In view of the state of the art, a need exists to provide an improved electrical insulating oil that overcomes the deficiencies of existing insulating oils.

It is an object of this invention to provide an electrical insulating substance that has an excellent dielectric constant, a good hydrogen gas absorbing capacity and a high compatibility with insulating or dielectric materials made of plastic.

It is another object of this invention to provide oil filled electrical appliances that have excellent corona discharge characteristics, dielectric breakdown voltage and maintain a long service life. The achievement of these and other objects will be apparent from the following description of the subject invention.

SUMMARY OF THE INVENTION

These and other objects are achieved by preparing an improved electrical insulating substance by dehydrogenating an aromatic hydrocarbon or hydrocarbons having aliphatic or alicyclic hydrocarbon residual group or groups having two or more carbon atoms and two condensed or two noncondensed aromatic nuclei.

In particular, this invention relates to an improved electrical insulating substance which comprises:

a dehydrogenation reaction mixture which is prepared by dehydrogenating a feedstock comprising an aromatic hydrocarbon having two condensed or two noncondensed aromatic nuclei and at least one aliphatic or alicyclic hydrocarbon substituent having two or more carbon atoms attached to the aromatic nuclei, said dehydrogenation reaction being conducted in the presence of a dehydrogenation catalyst under conditions effective to increase the bromine number by at least 0.4 cg/g relative to said number prior to dehydrogenation and to provide said dehydrogenation reaction mixture comprising at least 0.5% by weight of aromatic monoolefin or diolefin having two condensed or two noncondensed aromatic nuclei and at least 10% by weight of unreacted feedstock.

In another embodiment, this invention relates to an electrical appliance that contains the electrical insulating substances of the present invention.

In yet another embodiment, the electrical insulating substances are prepared by a method which comprises:

(a) dehydrogenating a feedstock comprising an aromatic hydrocarbon having two condensed or two noncondensed aromatic nuclei and at least one aliphatic or alicyclic hydrocarbon substituent having two or more carbon atoms attached to the aromatic nuclei in the presence of a dehydrogenation catalyst under conditions effective to provide a dehydrogenation reaction mixture comprising at least 0.5% by weight of aromatic monoolefin or diolefin having two condensed or two noncondensed aromatic nuclei and at least 10% by weight of unreacted feedstock; and (b) recovering the reaction mixture.

In another emodiment, this invention relates to electrical insulating oil prepared by the method described above.

DETAILED DESCRIPTION OF THE INVENTION

The present invention relates to an improved electrical insulating substance which contains an aromatic hydrocarbon having two condensed or two noncondensed aromatic nuclei. The aromatic hydorcarbon can be any compound in which at least one olefinic double bond in a molecule is produced by dehydrogenation. Stated another way, the aromatic hydrocarbon is a compound that has two condensed or two noncondensed aromatic nuclei and at least one aliphatic or alicyclic hydrocarbon substituent having two or more carbon atoms attached to the aromatic nuclei. These hydrocarbon substituents are mono-valent or poly-valent hydrocarbon groups that are derived from alkanes such as ethane, propane, butane, pentane, hexane, heptane, octane and cycloalkanes such as cyclopentane and cyclohexane. The mono-valent hydrocarbon groups are exemplified by ethyl, propyl, isopropyl, butyl, sec-butyl, isobutyl and the like. However, it should be noted that an aromatic hydrocarbon of about 500 or less in molecular weight is generally preferable because the dehydrogenation is, easily conducted and the electrical properties of obtained mixture are good.

The aromatic hydrocarbons are exemplified by diarylalkane, diarylcycloalkane, arylindane, alkylbiphenyl, cycloalkylbiphenyl, alkylnaphthalene and cycloalkylnaphthalene.

The diarylalkane and diarylcycloalkane are exemplified by 1,1-diarylalkanes such as 1,1-diphenylethane, 1-phenyl-1-tolylethane, 1-phenyl-1-xylylethane and 1-phenyl-1-ethylphenylethane; 1,2-diarylalkanes such as 1-phenyl-2-ethylphenylethane and 1-phenyl-2-isopropylphenylethane; and diphenylcyclohexane.

The alkylbiphenyl and cycloalkylbiphenyl are exemplified by monoisopropylbiphenyl, diisopropylbiphenyl and cyclohexylbiphenyl.

The alkynnaphthalene and cycloalkynnaphthalene are exemplified by ethylnaphthalene, isopropylnaphthalene and diisopropylnaphthalene.

The hydrocarbon feed for preparing the electrical insulating substance of this invention can be any hydrocarbon fraction containing the above defined diaromatic hydrocarbon. For example, a fraction containing the diaromatic hydrocarbons that is derived from a process to prepare the above diaromatic hydrocarbon can be employed.

In one of the preferred embodiments of this invention, a fraction containing diarylalkanes as by-products, that can be obtained in the alkylation process to prepare alkylated aromatic hydrocarbons serves as the dehydrogenation feed. More particularly, this fraction is obtained by alkylating aromatic hydrocarbons with an alkylating agent in the presence of an alkylation catalyst to obtain an alkylation product containing mono- and polyalkylated aromatic hydrocarbons, diarylalkanes, heavier products, and unreacted materials. The mono- and polyalkylated mono-aromatic hydrocarbons and unreacted materials from the above-obtained alkylation product are separated to provide a fraction that contains diarylalkanes.

For the above alkylation reaction, various aromatic hydrocarbons and alkylating agents can be used. For example, if raw materials produce alkylated aromatic hydrocarbons, diarylalkanes and heavier products such as polyaromatic hydrocarbons, and the diarylalkanes thus obtained can be converted into olefins such as monoolefins and diolefins by dehydrogenation, such raw materials can also be used as the alkylation feedstock.

Accordingly, exemplary raw materials are benzene; alkylbenzenes such as toluene and xylene; and partially hydrogenated condensed polyaromatic hydrocarbon such as indane.

The alkylating agents are exemplified by ethylene, propylene and butene; alkanols such as ethanol, propanol and butanol; and halogenated paraffin such as ethyl chloride.

In the alkylation reaction, specific hydrocarbons and alkylating agents are selected and used. Additionally, any conventional alkylation catalysts are considered to be within the scope of this invention. For example, Friedel-Crafts catalysts such as aluminum chloride, mineral acids such as sulfuric acid, organic acids such as p-toluenesulfonic acid, super acids such as trifluoromethane sulfonic acid, and solid catalysts such as silica alumina and zeolite can be employed.

After the alkylation reaction, unreacted material such as benzene, and mono-alkylated and polyalkylated monoaromatic hydrocarbons as well as heavier products, are separated from the alkylation product and dehydrogenation is then carried out with the recovered fraction containing diarylalkanes.

Since the alkylation process is carried out on an industrial scale, these by-products are obtained in large quantities and at low cost. This process is preferred because the reaction mixture that results produces a fraction that contains diarylalkanes with superior electrical properties characteristic of the present invention.

The alkylation of benzene or toluene with ethylene can be accomplished by any known methods. For example, liquid phase alkylation method or the gas phase alkylation can be utilized.

The molar ratio of benzene to ethylene is in the range of about 25:1 to 2:1, preferably from about 10:1 to 3:1. Alkylation catalysts, such as solid catalysts, mineral acids, and Friedel-Crafts catalysts are preferably employed. These catalysts are exemplified by alumina, silica-alumina, zeolite, sulfuric acid, hydrofluoric acid, phosphoric acid, sulfonic acid, p-toluene sulfonic acid, and aluminum halides such as aluminum chloride, aluminum bromide, zinc chloride, iron chloride and boron fluoride.

In a liquid phase reaction, the reaction temperature is in the range of about 20° to about 175° C, preferably about 90° to about 150° C. The reaction pressure is any value that is sufficient to maintain a reaction mixture in a liquid state, for example, from about 0.5 to about 14 kg/cm$^2$. The reaction time is generally in the range of about 10 minutes to about 10 hours, preferably about 20 minutes to about 3 hours.

In the gas phase reaction, available catalysts are phosphoric acid carried on diatomaceous earth, silica, alumina, or aluminum silicate, and solid catalysts such as alumina carried on silica gel. The reaction temperature is in the range of about 250° to about 450° C, preferably about 300° to about 400° C, with the reaction pressure in the range of about 25 to about 85 kg/cm$^2$, preferably about 42 to about 70 kg/cm$^2$.

The alkylation product obtained from the above reactions contains unreacted materials, such as benzene and ethylene, mono- and polyethylbenzene, 1,1-diphenylethane, 1-phenyl-1-ethylphenylethane, 1,1-di(ethylphenyl)ethane and heavier products. The alkylation product is then subjected to usual steps of settling and filtration known to those skilled in the art to remove any alkylation catalysts such as an aluminum chloride catalyst. The filtrate then is rinsed with water and neutralized.

After rinsing and neutralizing the filtrate, the unreacted benzene and mono-aromatic hydrocarbons such as ethylbenzene and polyethylbenzene are removed from the alkylation product as the overhead through any conventional method such as distillation. The fraction remaining contains an asphaltic substance that may be used as fuel or the like. This asphaltic substance is then removed by any conventional separation process, i.e. distillation, as a bottom fraction while the remaining fraction which contains diarylalkanes is subjected to dehydrogenation in accordance with the process of this invention.

In the case of alkylation of benzene or toluene with ethylane, this diarylalkane-containing fraction which will serve as the dehydrogenation feedstock has boiling points in the range of about 255° to about 420° C, preferably about 260° to about 400° C, and more preferably about 268° to about 400° C. The substances contained in this resulting fraction with this boiling range are 1,1-diphenylethane, 1-phenyl-1-ethylphenylethane, 1,1-di(ethylphenyl)ethane, and heavier diarylalkanes.

Any refining treatment, such as neutralization, to remove the residue of the alkylation catalyst can be carried out before or after the dehydrogenation. This refining treatment is done by using an appropriate organic or inorganic basic substance. The basic substances are exemplified by Group I alkali metals, and Group II alkaline earth metals as well as their corresponding oxides and hydroxides. More particularly, lithium, sodium, postassium, magnesium, calcium, strontium and barium, as well as their corresponding hydroxides are preferred. The refining treatment can be performed in any conventional manner, as well as using the above matallic oxide in the aforementioned distillation step. Further, the refining treatment can be carried out by using absorbents such as clay, silica, alumina and silica alumina.

The feed stock of the present invention such as diarylalkane-containing fraction is dehydrogenated in the presence of a catalyst, in which any known dehydrogenation catalyst can be utilized. For instance, exemplary of these catalysts are oxides of metals such as chromium, iron, copper, potassium, magnesium and calcium, precious metals such as platinum and palladium, or those metal oxides or precious metals that are supported on a carrier of alumina or the like.

The reaction temperature of dehydrogenation reaction is in the range of about 350° to about 650° C, preferably about 400° to about 600° C. When the dehydrogenation is carried out through a continuous fixed bed process, the LHSV (liquid hourly space velocity) is in the range of about 0.2 to about 10, preferably about 0.5 to about 3.0.

The reaction pressure is not especially limiting since the molar number increases in dehydrogenation. Pressures from a reduced pressure to about atmospheric pressure are sufficient.

In the dehydrogenation reaction, any inert gas such as steam can be introduced into the reaction system. Further, if necessary, a suitable diluent can be utilized. However, when the rate of dehydrogenation is not high, the hydrocarbon feed conveniently serves as a diluent.

In the dehydrogenation process of this invention, the above catalysts and reaction conditions are selected in order to suppress the occurrence of side effects such as cracking (decomposition) or polymerization. However, it is necessary that the dehydrogenation must be so carried out as to produce more than about 0.5 wt %, preferably more than 5.0 wt % of the aromatic monoolefin or diolefin having two condensed or two noncondensed aromatic nuclei in the dehydrogenation reaction mixture. When the content of the above aromatic olefin is less than 0.5 wt %, this invention cannot be expected to be effective.

In the dehydrogenation reaction, the obtained dehydrogenation reaction mixture contains various aromatic olefins. Since it is inconvenient to determine the contents of these various aromatic olefins, it is generally advantageous that the bormine number (cg/g) of the hydrocarbon feed be determined as the indicator of the content of aromatic olefins. Thus, when the weight percent of the aromatic olefins in the dehydrogenation product is 0.5 wt % or higher, the bromine number of the hydrocarbon feed is raised at least 0.4 cg/g, preferably more than 4.0 cg/g, as compared with the value before the dehydrogenation.

The complete dehydrogenation of the resulting fraction is not desirable because it is generally difficult to accomplish and is accompanied by decomposition as well as polymerization at higher conversion rates. Accordingly, it is not desirable for complete dehydrogenation to take place. Additionally, complete dehydrogenation would effectively negate the synergistic effect produced by the olefins and unreacted starting materials. For example, it is necessary that at least 10% by weight, preferably more than 17% by weight of unreacted starting material remain after dehydrogenation for the synergistic effect to manifest itself. Where the unreacted starting material in the product is less than 10% by weight, the synergistic effect cannot be effected and the product is liable to be unstable when used as an electrical insulating oil.

Further, heavier components produced by polymerization and lighter-aliphatic or cycloaliphatic components produced by decomposition are not useful in the present invention. However, aromatics having two aromatic nuclei which can be produced by partial decomposition, are desirable components in the present invention, because of the synergistic effect among produced olefins and unreacted starting material.

Therefore, after the reaction, hydrogen, and if necessary, lighter components such as aliphatic or cycloaliphatic hydrocarbons produced by side reaction such as decomposition and heavier components produced by polymerization are removed by distillation, thereby obtaining a dehydrogenation reaction mixture which is the electrical insulating substance of this invention.

In another embodiment of this invention, an electrical insulating oil can be prepared which possesses superior electrical properties.

If the dehydrogenation reaction mixture described above has a proper viscosity and the proper content of aromatic olefins, the dehydrogenation reaction mixture can be used as an electrical insulating oil without further processing. However, if the viscosity is too high or the content of the aromatic olefins is too large, the dehydrogenation reaction mixture should be mixed with a quantity of a conventional electrical insulating oil or oils to provide an electrical insulating oil with superior electrical properties. Further, when the above electrical insulating substance is a solid material at ordinary temperatures but melts at elevated temperatures of usual impregnation, the electrical insulating substance can be utilized by heating and fusing it for impregnation. Alternatively, the electrical insulating substance can be dissolved in any suitable electrical insulating oil having dissolving power to provide an electrical insulating oil in accordance with this invention.

Additionally, the aromatic olefins prepared by dehydrogenation can be isolated through any conventional separation process such as distillation, extraction or recrystallization. The boiling points of components are close to each other and any undesirable effect such as polymerization of the aromatic olefins is minimal. Thus, the electrical appliances made by using the dehydrogenation reaction mixture have excellent electrical performance because of the synergistic effect. Accordingly, it is preferred that the electrical insulating oil be prepared by using the electrical insulating substance of this invention without the aforementioned isolation process. Therefore, it is preferable to use the dehydrogenation reaction mixture alone or the combination of the mixture with other electrical insulating oils.

If the electrical insulating substance of the invention can be dissolved, any quantity of the following conventional electrical insulating oils can be mixed together. Such insulating oils are exemplified by mineral oils, olefin oligomers such as polybutene, alkyl-or cycloalkylbenzenes such as dodecylbenzene and dicyclohexylbenzene, animal and vegetable oils such as castor oil as a triglyceride, phthalic esters such as dioctylphthalate, and silicone oil.

In addition to the above electrical insulating oils, saturated compounds having two condensed or two noncondensed aromatic nuclei and aromatic olefins having at least two condensed or two noncondensed aromatic nuclei can be utilized by mixing them with the electrical insulating substance of this invention.

Saturated compounds having two condensed or two noncondensed aromatic nuclei are exemplified by diphenylmethane; lower alkyl derivatives of diphenylmethane such as benzyltoluene; 1,1-diphenylethane, 1,2-diphenylethane or their lower alkyl derivatives such as 1-phenyl-1-xylylethane, 1-phenyl-1-ethylphenylethane, 1-phenyl-1-tolylethane, 1-phenyl-1-isopropylphenylethane, 1-phenyl-1-trimethylphenylethane, 1,1-di(ethylphenyl)ethane, 1-phenyl-2-ethylphenylethane, 1-phenyl-2-isopropylphenylethane, and 1,2-dixylylethane; diarylalkanes and diarylcycloalkanes such as 1,3-diphenylbutane, 2,4-diphenyl-2-methylpentane and diphenylcyclohexane; alkylarylindane such as methylphenylindane; biphenyl; alkylor cyclo-hexylbiphenyl; alkylnaphthalenes such as mono- or diisopropylnaphthalene; ethers such as ditolyl ether, dixylylether, dibenzyl ether, bis ($\alpha$-methyl-benzyl)ether and diarylthioether; and triarylalkanes such as dibenzyltoluene, distyrenated xyxlene, bisphenetyltoluene, terphenyl, styrenated naphthalene, and triphenylhexane.

The above-mentioned aromatic olefins having at least two condensed or two noncondensed aromatic nuclei are exemplified by 1,1-diphenylethylene; stilbene; unsatureated dimers or trimers of styrenes including styrene, vinyltoluene, $\alpha$-methylstyrene and isopropenyltoluene, such as 1,3-diphenylbutene-1, and 2,4-diphenyl-4-methylpentene-1; vinylphenyl-phenylalkanes and their lower alkyl derivatives such as 1-vinylphenyl-1-phenylethane, 1-isopropenylphenyl1-phenylethane and vinylphenyl-phenylmethane; and other aromatic monoolefins such as isopropenylbiphenyl and isopropenylnaphthalene.

A mixture of one or more of the above known insulating oils can be utilized in combination with the dehydrogenation reaction mixture of this invention.

The oxidation stability of the electrical insulating substance of this invention can be improved by the addition of several known antioxidants to the insulating substance of this invention. Exemplary of such antioxidants, are phenol compounds like 2,6-di-tert-butyl-p-cresol, 2,2'-methylenebis(4-methyl-6-tert-butylphenol), 4,4'-butylidenebis (3-methyl-6-tert-butylphenol), 4,4'-thiobis(3-methyl-6-tert-butylphenol), stearyl-$\beta$-(3,5-di-tert-butyl-4-hydroxyphenol) propionate, tetrakis[methylene-3(3', 5'-di-tert-butyl-4'-hydroxyphenyl)-propionate]methane, 1,3,5-trimethyl-2,4,6-tris (3,5-di-tert-butyl-4-hydroxybenzyl)benzene, and 1,1,3-tris(2-methyl-4-hydroxy-5-tert-butylphenol)butane; sulfur compounds such as dilauryl thiodipropionate, distearyl thiodipropionate, laurylstearyl thiodipripionate, and dimyristyl thiodipropionate; and phosphorous compounds such as thiisodecylphosphite, diphenylisodecylphosphite, triphenylphosphite, and trinonylphenylphosphite.

These antioxidants can be added to the electrical insulating substance singly or in combination of two or more different kinds. The antioxidant should be added to the electrical insulating substance from about 0.001 to about 5% by weight, preferably from about 0.01 to about 2.0% by weight.

Further, in order to impart a nonflammable property and other desirable effects to the electrical insulating substance of this invention, several known additives, such as phosphoric esters and epoxy compounds, can be added to the electrical insulating substance.

When the electrical insulating substance of this invention is utilized as an electrical insulating oil, it shown excellent compatibility with insulating materials made of plastics such as polyolefins. Accordingly, when the electrical insulating substance is used for impregnating oil-filled electrical appliances having dielectric or insulating materials partially or totally made of plastics, high-tension, light-weight and long-life electrical appliances can be provided. Further, the electrical insulating substance of this invention can be mixed with or dissolved in known electrical insulating oils including hydrocarbons having at least two condensed or two noncondensed aromatic nuclei such as diarylalkanes, alkylbiphenyls and alkylnaphthalenes. Further, similar advantages can be attained with the synergistic effect of the combined components as described above.

Accordingly, the electrical insulating substance of this invention, or the electrical insulating oil containing the same, is suitable for use as an electrical insulating oil for general uses and is especially suitable for use in impregnation of oil-filled electrical appliances such as capacitors, oil-filled power cables and transformers.

As described at the beginning of this specification, the requirements of high-voltage withstanding and size reduction of such oil-filled electrical appliances have become severe in recent years. In order to meet these requirements, plastics are used to replace either partially or totally the conventional insulating paper as insulating materials or dielectric materials for the oil-filled electrical appliances. More particularly, as electrical insulating materials (dielectric materials) of electric capacitors, there is proposed the use of a combination of insulating paper and plastic films. As the plastic films, stretched or nonstretched polypropylene, polymethylpentene, polyester, polyvinylidene fluoride and polycarbonate films can be used. The use of these plastic films singly, the use of the embossed films of these plastic films to facilitate impregnation with the insulating oil, or the use of singleside or double-side metallized plastic films, where the metallic layer serves as an electrode, is also possible. In oil-filled cables, the electrical insulating materials are made of polyolefin films such as cross-linked or non-cross-linked polyethylene film, stretched or nonstretched polypropylene film, and polymethylpentene film; paper-polyolefin laminated film made by the extrusion of polyolefin onto paper; composite film that is made by cross-linking insulating paper with silane-grafted polyethylene in the presence of a silanol condensation catalyst; or an artificial paper sheet that is made by mixing wood pulp and polyolefin fiber.

An electric capacitor is often provided with insulating (dielectric) material that is partially or totally made of plastics, especially polyolefin. The capacitor is then impregnated with the electrical insulating oil (including the electrical insulating substance itself) of the present invention resulting in the insulating material being can be fully and completely impregnated with the electrical insulating oil. This results in a slight swelling of the insulating material and voids (unimpregnated portions) are not formed. Accordingly, corona discharge due to the convergence of electric fields to the voids rarely occurs, and dielectric insulating oil of this invention has excellent hydrogen gas absorbing capacity and corona discharge resistance under high-voltage stress, so that it is possible to have both a long service life and high-voltage use of the electrical appliances.

In the case of electric power cables, a change in dimensions of the insulating material due to swelling is minimal, and resistance to the insulating oil flow can be minimized so that oil impregnation can be performed in a relatively short period. It should be understood that, because of the ease of impregnation, voids are rarely formed and the dielectric breakdown voltage becomes higher. When a cable is made by using an insulating material of a laminated film or composite film made of plastic material and paper, peeling, creasing and buckling of the insulating material upon bending of the cable do not occur even when the insulating material has been in contact with the electrical insulating oil for a long time. Further, as is the case of the electric capacitor, a power cable having a good corona discharge resistance can be obtained due to the excellent hydrogen gas absorbing capacity of the electrical insulating oil. Accordingly, it is also possible to obtain a long service life and high-voltage use, as with capacitors.

Accordingly, the advantageous features of this invention can be improved by impregnation with the electrical insulating oil consisting of a plurality of specific component materials, owing to the synergistic effect between the component materials. Further, the excellent electrical characteristics, biodegradability, thermal resistance, and oxidation stability of each component material can be well maintained, and at the same time, the viscosity and pour point of the electrical insulating oil composition can be adjusted within desired ranges. Therefore, the manufacture of oil-filled electrical appliances is facilitated, and oil-filled electrical appliances exhibiting high performance under any use conditions can be obtained.

The following examples are presented as specific embodiments of the present invention and show some of the unique characteristics of the present invention and are not to be considered as constituting a limitation on the present invention.

EXAMPLE 1

Monoisopropylbiphenyl was dehydrogenated in the presence of a catalyst and steam under the following conditions and obtained an electrical insulating substance (bromine number: 41.8 cg/g) containing 51 wt % of monoisopropenylbiphenyl.

| Conditions of Dehydration: | |
|---|---|
| Catalyst: | Iron oxide catalyst containing promoters of potassium carbonate and chromium oxide Trade mark: G64A, made by Nissan Girdler Catalyst Co., Ltd. Particle size: 14–28 mesh |
| Temperature: | 590° C. |
| LHSV: | 1.0 |
| $H_2O$/Starting Material (by weight): | 3.0 |
| Pressure: | Atmospheric pressure |

In the next step, the dehydrogenation reaction mixture was diluted by the starting material of monoisopropylbiphenyl, thereby preparing an electrical insulating oil (bromine number: 8.2 cg/g) containing 10 wt % of monoisopropenylbiphenyl.

Capacitors were impregnated with this electrical insulating oil and the starting material of monoisopropylbiphenyl, respectively. The performances of both kinds of the capacitors were compared.

The capacitors were made by winding two-ply capacitor use polypropylene film (each 14 $\mu$ thickness) as dielectric material and aluminum foil as electrode. The capacitance of the obtained capacitor after impregnation was about 0.4 $\mu$F.

EXAMPLE 2

Dehydrogenation was carried out by using 1-phenyl-1xylylethane in like manner as Example 1 except that the reaction temperature was 420° C, to obtain a reaction mixture of electrical insulating substance (bromine number: 7.6 cg/g) containing 10 wt % of 1-phenyl-1-xylylethylene. Capacitors that were made in like manner to that of Example 1 were impregnated with the above-obtained electrical insulating substance and the 1-phenyl-1-xylylethane, respectively, and the performance of both of the capacitors were compared.

EXAMPLE 3

Dehydrogenation was carried out by using diisopropylnaphthalene in like manner to that of Example 1, except that the reaction temperature was 500° C, to obtain a dehydrogenation reaction mixture of electrical insulating substance having a bromine number of 8.1 cg/g. Assuming that all olefins are monoolefins, this value correspondes to 10.6 wt % of olefins.

Capacitors were made through the procedure described below, and they were impregnated with the above electrical insulating substance and the starting material of diisopropylnaphthalene, respectively. The performances of both the capacitors were compared.

In the preparation of capacitors, capacitor-use polypropylene film (28 μ in thickness, 62 mm in width) and insulating paper (12 μ in thickness, 62 mm in width) were wound to form two-ply dielectric material. As electrodes, aluminum foil (7 μ in thickness, 50 mm in width) was wound. The capacitance of the obtained capacitors after impregnation was 0.7 μF.

In the performance tests, corona starting voltages (CSV), corona ending voltages, (CEV) and breakdown times under a fixed voltage were measured. The results of the tests are shown in Table I. In the tests for breakdown times, each value was calculated such that seven capacitors impregnated with the same oil were tested, and the maximum value and minimum value were neglected, and the average of the other five breakdown times was adopted as the resultant value. Furthermore, the breakdown times were represented by the values relative to the values of the starting materials for dehydrogenation.

Example 1. The performances of the capacitors were tested and the results of the tests are shown in Table II.

EXAMPLE 5

By using 1-phenyl-1-(4'-ethylphenyl)ethane, dehydrogenation was carried out as in Example 1, except that the reaction temperature was 550° C, to obtain a reaction mixture (bromine number: 75.3 cg/g) having the following composition.

| Compounds | wt % |
| --- | --- |
| 1-phenyl-1-(4'-ethylphenyl)ethane | 23.8 |
| 1-phenyl-1-(4'ethylphenyl)ethylene | 39.9 |
| 1-phenyl-1-(4'vinylphenyl)ethane | 5.0 |
| 1-phenyl-1-(4'vinylphenyl)ethylene | 28.1 |
| Others | 3.2 |
| Total | 100.0 |

By using an electrical insulating oil (bromine number: 7.5 cg/g) containing 10 parts by weight of this reaction mixture and 90 parts by weight of 1-phenyl-1-xylylethane, capacitors were made as in Example 1. The performances of the capacitors were tested and the test results are shown in Table II. The values on breakdown times in Table II are all relative values with respect to the value in which the basic oil, 1-phenyl-1-xylylethane, is singly used.

It will be understood from the results shown in Table I and II that the electrical insulating substance of this invention obtained by dehydrogenation can be used as it stands or in a mixture with other electrical insulating oils, and it exhibits excellent electrical properties.

In other words, the aromatic hydrocarbons used as

TABLE I

| Example No. | Impregnating Oil | Kinematic Viscosity (cSt at 30° C.) | CSV (kV) | CEV (kV) | Breakdown Time (Relative Value) |
| --- | --- | --- | --- | --- | --- |
| 1 | Monoisopropylbiphenyl | 6.15 | 2.6 | 2.1 | 1.0 |
|   | Monoisopropylbiphenyl plus dehydrogenation product (10 wt % monoisopropenylbiphenyl) | 6.18 | 3.1 | 2.5 | 18.0 |
| 2 | 1-phenyl-1-xylylethane | 6.54 | 2.8 | 2.2 | 1.0 |
|   | Dehydrogenation product (10 wt % 1-phenyl-1-xylylethylene) | 6.55 | 3.2 | 2.6 | 18.5 |
| 3 | Diisopropylnaphthalene | 9.72 | 1.9 | 1.1 | 1.0 |
|   | Dehydrogenation product | 9.79 | 2.9 | 2.1 | 25.4 |

EXAMPLE 4

Dehydrogenation was carried out by using 1,1diphenylethane as in Example 1, except that the reaction temperature was 575° C, to obtain a reaction mixture (bromine number: 73.1 cg/g) containing 83 wt % of diphenylethylene.

By using an electrical insulating oil (bromine number: 7.3 cg/g) containing 10 parts by weight of this reaction mixture and 90 parts by weight of 1-phenyl-1-xylylethane, capacitors were made in like manner to that of the starting material of dehydrobenation in the foregoing examples are used as electrical insulating oils and are regarded as suitable for use in the impregnation of oil-filled capacitors and power cables containing at least partly plastic materials. It will be apparent, however, that using the electrical the electrical insulating oils insulating substance of the present invention are superior to these oils.

TABLE II

| Example No. | Impregnating Oil | | | | Kinematic Viscosity (cSt at 30° C.) | CSV (kV) | CEV (kV) | Breakdown Time (Relative Value) |
| --- | --- | --- | --- | --- | --- | --- | --- | --- |
| | Aromatic Hydrocarbon | wt % | Aromatic Olefin | wt % | | | | |
| 4 | 1-Phenyl-1-xylylethane | 90 | Dehydrogenation product of Ex. 4 | 10 | 6.12 | 3.2 | 2.6 | 19.3 |
| 5 | 1-Phenyl-1-xylylethane | 90 | Dehydrogenation product of Ex. 5 | 10 | 6.33 | 3.3 | 2.7 | 25.6 |

EXAMPLE 6

In a process for preparing ethylbenzene, which is used for production of polystyrene, benzene was reacted with ethylene in the presence of an aluminum chloride catalyst. From the alkylation product in this process, unreacted benzene, ethylbenzene and polyethylbenzene were distilled off by reduced pressure distillation to obtain a fraction (bromine number: 0.9 cg/g) having a boiling range of 260° to 310° C. (normal pressure).

The main components in this fraction were 37 wt % of 1,1-diphenylethane and 32 wt % of 1-ethtylphenylethane. Besides them, 1,1-di(ethylphenyl)ethane, tetralin, indane, naphthalene, fluorene, their alkyl derivatives, and unknown substances were also contained in the fraction.

The recovered fraction was dehydrogenated in the presence of a catalyst and steam under the following conditions.

| | |
|---|---|
| Catalyst: | Iron oxide catalyst containing promotors of potassium carbonate and chromium oxide Trade mark: G64A, made by Nissan Girdler Catalyst Co., Ltd. |
| Temperature: | 500° C. |
| LHSV: | 1.0 |
| $H_2O$/Starting Material: | 3.0 (molar ratio) |
| Pressure: | Atmospheric pressure |

After the dehydrogenation, lighter components and heavier components were removed to obtain a dehydrogenation mixture. The bromide number of this dehydrogenation mixture was 15.3 cg/g. Assuming that contained olefins are all monoolefins, this value corresponds to about 19 wt % in olefin content. This dehydrogenation mixture was used as an electrical insulating oil for the following capacitor tests.

The dehydrogenation mixture and the foregoing recovered fraction before dehydrogenation were used as electrical insulating oils and capacitors were impregnated with them as in Example 1. The performance of the capacitors were evaluated by corona starting voltages (CSV), corona ending voltages (CEV) and breakdown times.

The capacitors were made by winding two-ply capacitor use polypropylene film (each 14 μ thickness) as dielectric material and aluminum foil as electrodes. The capacitance of the obtained capacitors after impregnation was 0.4 μF. The breakdown times were represented by values relative to those of the recovered fraction before dehydrogenation. In the capacitor tests, 0.2 wt % of BHT as an antioxidant was added to both the oils. The results are shown in the following Table III.

TABLE III

| Impregnation Oil | CSV (kV) | CEV (kV) | Breakdown Time (Relative Value) |
|---|---|---|---|
| Recovered Fraction before Dehydrogenation | 2.6 | 2.0 | 1 |
| Dehydrogenation Product | 3.1 | 2.5 | 16.3 |

EXAMPLE 7

To a stainless steel-made continuous reaction vessel was added 100 g of synthetic zeolite ZSM-5 [$H^+$-type, $SiO_2/Al_2O_3$ (molar ratio) =60]and toluene was alkylated with ethylene under the following conditions:
Reaction temperature: 450° C
Reaction pressure: Atmospheric
Ethylene/toluene (mole): 0.2
W H S V: 4.5

The obtained reaction mixture was distilled and the fractions of boiling points below 250° C containing unreacted toluene, ethyltoluene and polyethyltoluene were distilled off to obtain heavier products in a yield of 2.1%.

The heavier components were then distilled under reduced pressure to obtain a fraction (A) having a boiling range of 275° to 320° C (atmospheric pressure). According to analysis of this fraction (A), it mainly contained diarylalkanes. The composition and properties are shown in the following analytical composition:

| | |
|---|---|
| Diarylalkanes ($C_nH_{2n-14}$) | 85.0% by weight |
| (n = 14) | (15.3%) |
| (n = 15) | (43.8%) |
| (n = 16) | (25.9%) |
| Others | 15.0% |
| Total | 100.0% |
| Properties: | |
| Bromine number | 0.05 cg/g |
| Viscosity | 4.6 cSt (at 40° C.) |

The recovered fraction was dehydrogenated in the same way as in Example 6. The bromine number of this dehydrogenation mixture was 13.5 cg/g. This value correspondes to about 18 wt % in olefin content. This dehydrogenation mixture was used in an electrical insulating oil for the same capacitor tests as Example 6. The results are shown in the following Table IV.

TABLE IV

| Impregnation Oil | CSV (kV) | CEV (kV) | Breakdown Time (Relative Value) |
|---|---|---|---|
| Recovered Fraction before Dehydrogenation | 2.4 | 1.9 | 1 |
| Dehydrogenation Mixture | 3.0 | 2.3 | 14.2 |

ELECTRICAL CHARACTERISTICS TEST

With regard to the electrical insulating oils of this invention that were used for the impregnation in the foregoing Examples 1 to 7, respectively, some electrical characteristics as insulating oils were measured. The results are shown in Table V.

TABLE V

| | Electrical Characteristics | | |
|---|---|---|---|
| Example No | $\epsilon$ at 80° C. | Tan δ %, at 80° C. | $\rho$ Ωcm, at 80° C. |
| 1 | 2.52 | 0.019 | $9.1 \times 10^{14}$ |
| 2 | 2.51 | 0.017 | $8.9 \times 10^{14}$ |
| 3 | 2.56 | 0.021 | $0.4 \times 10^{14}$ |
| 4 | 2.51 | 0.019 | $8.8 \times 10^{14}$ |
| 5 | 2.50 | 0.002 | $9.3 \times 10^{14}$ |
| 6 | 2.49 | 0.023 | $9.0 \times 10^{14}$ |

TABLE V-continued

| | Electrical Characteristics | | |
|---|---|---|---|
| Example No | ε at 80° C. | Tan δ %, at 80° C. | ρ Ωcm, at 80° C. |
| 7 | 2.48 | 0.022 | $9.0 \times 10^{14}$ |

Obviously, other modifications and variations of the present invention are possible in the light of the above teachings. It is therefore to be understood that changes may be made in the particular embodiments of this invention which are within the full intended scope of the invention as defined by the appended claims.

What is claimed is:

1. A method of preparing an electrical insulating compositin which comprises:
   (a) alkylating at least one aromatic hydrocarbon with an alkylating agent in the presence of an alkylating catalyst to produce an alkylation product, said alkylation product comprising unreacted substances, mono and polyalkylated aromatic hydrocarbons, diarylalkanes and heavier products;
   (b) recovering a fraction comprising diarylalkanes as a feedstock;
   (c) dehydrogenation said feedstock in the presence of a dehydrogenation catalyst under conditions effective to provide a dehydrogenation reaction mixture comprising at least 0.5% by weight of aromatic monoolefin or diolefin having two condensed or two noncondensed aromatic nuclei and at least 10% by weight of unreacted feedstock and to provide a bromine number of said dehydrogenation reaction mixture which is at least 0.4 cg/g higher than the bromine number of said feedstock; and
   (d) recovering said reaction mixture.

2. A method as defined in claim 1, wherein the aromatic hydrocarbon is benzene or toluene and the alkylating agent is ethylene.

3. A method as defined in claim 1, wherein said alkylation is carried at temperatures of about 20 to about 175° C.

4. A method as defined in claim 1, wherein said alkylation catalyst is a zeolite catalyst or aluminum chloride catalyst.

5. A method as defined in claim 1, wherein said fraction containing diarylalkanes has a boiling point of about 255° to about 420° C.

* * * * *

UNITED STATES PATENT AND TRADEMARK OFFICE
CERTIFICATE OF CORRECTION

PATENT NO. : 4,681,980
DATED : July 21, 1987
INVENTOR(S) : Atsushi Sato, et al.

It is certified that error appears in the above-identified patent and that said Letters Patent is hereby corrected as shown below:

Column 12, line 53: "that using the electrical the electrical insulating oils insulating substance" should read as --that the electrical insulating oils using the electrical insulating substance--

Column 13, line 14: "1-ethtylphenylethane" should read as --1-phenyl-1-ethylphenylethane--

Column 15, line 16, Claim 1: "compositin" should read as --composition--

Signed and Sealed this

Twenty-third Day of February, 1988

*Attest:*

DONALD J. QUIGG

*Attesting Officer*  *Commissioner of Patents and Trademarks*